(12) United States Patent
Dong

(10) Patent No.: US 7,806,826 B2
(45) Date of Patent: Oct. 5, 2010

(54) METHOD AND APPARATUS FOR ELIMINATING ABNORMAL BLOOD FLOW VELOCITIES IN A COLOR FLOW IMAGE

(75) Inventor: Yongqiang Dong, Nanshan (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 1115 days.

(21) Appl. No.: 11/317,954

(22) Filed: Dec. 22, 2005

(65) Prior Publication Data

US 2007/0083112 A1    Apr. 12, 2007

(30) Foreign Application Priority Data

Sep. 29, 2005    (CN) .................. 2005 1 0100147

(51) Int. Cl.
*A61B 8/06*    (2006.01)
(52) U.S. Cl. .................. 600/454; 600/453; 600/465; 600/468
(58) Field of Classification Search ......... 600/453–455, 600/437, 465, 468
See application file for complete search history.

(56) References Cited

U.S. PATENT DOCUMENTS

| | | | |
|---|---|---|---|
| 5,042,491 A | 8/1991 | Amemiya | |
| 5,215,094 A | 6/1993 | Franklin et al. | |
| 5,357,580 A | 10/1994 | Forestieri et al. | |
| 5,467,770 A | 11/1995 | Smith et al. | |
| 5,515,852 A | 5/1996 | Karp et al. | |
| 5,653,234 A | 8/1997 | Kim et al. | |
| 5,860,928 A * | 1/1999 | Wong et al. | 600/453 |
| 5,860,930 A | 1/1999 | Guracar | |
| 5,897,502 A | 4/1999 | Wong et al. | |
| 6,309,357 B1 * | 10/2001 | Guracar et al. | 600/454 |
| 6,571,020 B1 * | 5/2003 | Dumoulin et al. | 382/254 |
| 6,663,567 B2 * | 12/2003 | Ji et al. | 600/455 |
| 7,371,219 B2 * | 5/2008 | Sakaguchi et al. | 600/455 |
| 2007/0161900 A1 * | 7/2007 | Hagiwara | 600/454 |

FOREIGN PATENT DOCUMENTS

CN    1142348 A    12/1997

* cited by examiner

*Primary Examiner*—Ruth S Smith
*Assistant Examiner*—Christopher Cook
(74) *Attorney, Agent, or Firm*—Kory D. Christensen; Stoel Rives LLP

(57) ABSTRACT

A method for eliminating abnormal blood flow velocities in an ultrasonic imaging system is provided in present invention. The method comprises: receiving signals of blood flow; preprocessing the received signals to generate velocity signs in real time; obtaining a plurality of the velocity signs in a predefined spatial and temporal order, and performing weighted smoothing on the plurality of the velocity signs; determining the direction of blood flow at the pixel to be confirmed according to result of the weighted smoothing. A module for performing above method and a color flow imaging system with such a module are also provided in present invention. The method and apparatus provided by present invention can judge the practical direction of blood flow intelligently by performing spatial-temporal smoothing only on the signs of blood flow velocities, so that the estimation error caused by the system noise, clutter residue, speckle effect and etc. can be corrected.

23 Claims, 5 Drawing Sheets a                          b

METHOD AND APPARATUS FOR ELIMINATING ABNORMAL BLOOD FLOW VELOCITIES IN A COLOR FLOW IMAGE

FIELD OF THE INVENTION

The present invention relates to an ultrasonic diagnostic method and apparatus. Specifically, this invention relates to method and apparatus for ultrasonic color flow imaging, and more particularly relates to a method and apparatus, which is capable of eliminating the pixels indicating abnormal blood flow velocities during the color flow imaging process.

BACKGROUND OF THE INVENTION

In ultrasonic diagnostic system, color flow imaging technology is used to measure the moving status and parameters of blood flow or the tissues within a human body, which includes the direction and speed of blood flow, strength of blood flow and the turbulence associated with the blood flow. And the blood flow status will be displayed with pseudo-color on the screen to help doctor make a correct diagnosis.

The basic principle of color flow imaging technology is based on ultrasound Doppler effect to detect the status of the moving subject. When blood flow within a living subject is subjected to ultrasonic waves sending from the probe, the ultrasonic waves are reflected, refracted, absorbed and backscattered. Because the tissue or blood flow is moving, the frequency of the backscattered waves changes from that of the transmitted waves due to the Doppler effect. For example, the frequency of the received waves from the blood flow moving toward the probe (normally indicated in red in the color flow images) increases, while the frequency of the received waves from the blood flow moving backward (normally indicated in blue) decreases. Therefore, the speed and direction of blood flow can be determined by measuring the phase difference between the received waves and transmitted waves, and then the blood flow status can be displayed on the screen. However, in practical applications, the direction of blood flow velocity, which is calculated by measuring the received waves, always shows abnormities due to various kinds of reasons. For example, blue pixels appear in the blood vessel images while the flow is indicated in red, or red pixels appear in the blood vessel images while the flow is indicated in blue (except the turbulence phenomenon due to maximum Doppler detection limit). Thus, these abnormities will influence the clinical diagnosis.

System noise is regarded as the most intuitionistic one in all kinds of reasons resulting abnormities in the calculation of blood flow direction. Since ultrasonic backscattered wave from blood flow is 40~50 db lower than that from tissues, as the probing area goes deeper, the amplifier gain has to increase to compensate the depth attenuation, the backscattered wave of blood flow from far field will be immersed in the noise induced by the increasing amplifier gain, thereby causing the calculated direction of blood flow velocity to be abnormal.

Speckle effect is also one of the reasons resulting abnormities in the calculation of blood flow velocity. Speckle effect comes from that quite a lot of scatters may be included in one resolution cell and the phases of the reflected waves from these scatters are different when the backscattered waves arriving at the ultrasonic probe. Therefore, the amplitude of the backscattered waves in some resolution cells will be enhanced after the summation of the backscattered waves from all of the scatters. Whereas, the amplitude of the backscattered waves in some other resolution cells will be weakened after the summation. Under the same noise level, the signal to noise ratio of the weakened resolution cells becomes lower, so that it is easier to cause the calculated direction of blood flow velocity to be abnormal.

Another reason for resulting estimation error for the direction of blood flow velocity comes from the wall filter processing. In most commercial ultrasonic color imaging systems, a fixed cut-off frequency for the high pass filter can be usually selected as the low limit for detectable blood flow velocity, so as to suppress tissue reflected wave. However, the slowly moving velocity of tissue in a 2-D cross section is different from resolution cell to cell. When the cut-off frequency for the high pass filter cannot fit all resolution cells, the wall filtered signals from some resolution cells contain clutter residue. These clutter residual signals generally result estimation error for direction of blood flow velocity. In the vessel with low blood flow velocity, this phenomenon is more obvious.

The reasons resulting estimation error for the direction of blood flow velocity are not limited to above ones. Reverberation can also produce this kind of error. In order to eliminate the abnormal velocities in a color flow image as much as possible, several solutions are given in the art. Those solutions can be divided into two categories, i.e. spatial smoothing and temporal smoothing.

Therein, the methods for spatial smoothing include the one-dimensional smoothing along scan line presented in U.S. Pat. No. 5,042,491 and U.S. Pat. No. 5,653,234, and two-dimensional smoothing presented later in U.S. Pat. No. 5,515,852 and U.S. Pat. No. 5,860,928.

U.S. Pat. No. 5,042,491 discloses a solution for judging the direction of blood flow based on the strength and velocity of blood flow calculated by using auto-correlation algorithm, wherein this solution is directed to cancel the abnormities of blood flow velocities caused by the system noise. When one of or both of strength and velocity of blood flow is greater than a threshold in some resolution cells, the velocity estimation is regarded reliable and the output represents the sign of blood flow velocity. Otherwise the velocity estimation is regarded unreliable, and then the majority direction among the velocity directions of adjacent resolution cells along the scan line is used as the velocity direction of current resolution cells.

Additionally, U.S. Pat. No. 5,653,234 also discloses a solution for spatial smoothing to increase the autocorrelation coefficients or the signal-to-noise ratio of temporal samples, so as to enhance the reliability of velocity estimation. This solution firstly judges the strength of correlator's signals or temporal samples, signal changing speed and signal sum of absolute difference (SAD). When any one of these items meets certain condition, e.g., when the strength of temporal samples is greater than a threshold, the spatial smoothing aperture may be reduced, or even not be done. Otherwise the spatial smoothing aperture is enlarged.

U.S. Pat. No. 5,515,852 firstly discloses a solution utilizing weighted 2-D spatial smoothing to increase signal-to-noise ratio for estimating abnormal blood flow velocity. And it also provides different weighted solutions according to the distribution of strength and velocity estimated by using auto-correlation with regard to different parts of human body. Later, the solution disclosed in U.S. Pat. No. 5,860,928 also utilizes 2-D spatial smoothing to increase signal-to-noise ratio for detection. It differs from U.S. Pat. No. 5,515,852 in that the spatial smoothing is done only when the strength and speed of blood flow are greater than a certain threshold.

Temporal smoothing method firstly appears in the solution disclosed in U.S. Pat. No. 5,215,094. This solution enhances the signal-to-noise ratio in velocity estimation by using temporal recursive filtering. The methods disclosed in U.S. Pat. No. 5,357,580 and U.S. Pat. No. 5,467,770 is a kind of adaptive temporal recursive filtering. The former selects recursion factors according to the speed, while the later selects recursion factors according to the speed and the frame rate. The solution disclosed in U.S. Pat. No. 5,897,502 adds decision and threshold for velocity direction during temporal smoothing so as to enhance the ability for correcting the abnormities of velocity direction resulted by clutter residue and system noise. U.S. Pat. No. 5,860,930 discloses a solution utilizing the strength ratio of adjacent two frames to calculate the factor of temporal smoothing to obtain better image performance of blood flow.

The above two kinds of smoothing methods all attempt to eliminate abnormities in velocity estimation by utilizing the basic discipline of blood flow situation of human body so as to increase the quality of blood flow image. However, in the above existing technologies, spatial or temporal smoothing is performed separately. Therefore, the disadvantages of these prior arts are obvious:

1) Generally, in spatial smoothing methods, simple 2-D spatial smoothing is implemented on only one frame, without considering of the pulsation and periodicity of the blood flow, and thereby it is not sufficient to eliminate abnormities of blood flow velocities without any prior knowledge. Furthermore during 2-D spatial smoothing, unreliable speed value with abnormal direction is also used (for example, system noise may be regarded as reliable velocity even though its phase angle is random). Therefore, the smoothed velocity is unbelievable.

2) Though temporal smoothing considers pulsation and periodicity of blood flow, it requires more image frames of blood flow during a longer period to correct the abnormal blood flow velocities, or it requires to perform more reliable 2-D spatial smoothing for several times. But this kind of processing requires too much memory, then it cannot be realized or the cost will be too high.

Accordingly, since temporal and spatial smoothing is implemented separately in prior art, the conventional methods can not guarantee that pulsation and periodicity of blood flow (especially when frame rate of blood flow imaging is high) is considered during processing, so that these methods fails to eliminate the estimation error of blood flow velocity as desired.

Therefore, a decision method is required to judging the direction of blood flow accurately with high processing speed and low cost, and thereby the estimation error aroused by the factors such as system noise could be eliminated furthest.

SUMMARY OF THE INVENTION

An object of present invention is to provide a method and apparatus for eliminating abnormal blood flow velocities in a color flow image as much as possible in an ultrasonic color flow imaging system, so as to increase the precision and reliability of blood flow detection.

In order to realize the object, the inventor of present invention starts from existing technologies, and summarizes the basic discipline of blood flow in human body and the detection principle based on ultrasound Doppler effect as following items: a. the speed and direction of blood flow in human body possess certain periodicity and pulsation as systole and diastole; b. the changing of the direction of blood flow in normal human body is disciplinary during one cardiac cycle. When the geometry between the probe and the interrogated body is determined, the changing of blood flow direction in different applications presents different discipline during one cardiac cycle. The blood flow directions of most vessels keep unchanged substantially, while the blood flow directions of minority vessels will alternately change from forward to backward or vice versa, such as femoral artery; c. the phenomenon of sudden changes in the direction of pathological blood flow (turbulence) mainly appears under the condition of the blood flowing with high speed. In that case, it is characterized in that the strength of blood flow in a corresponding resolution cell is relatively high and may keep the same direction during continuous time frames; d. The phenomenon of overflow in blood flow velocity is an inherent disadvantage of pulsed wave ultrasonic Doppler detecting system. This phenomenon basically appears at the middle area of blood vessel (i.e. the area where blood flows at high speed). At the same time, the strength of blood flow in this corresponding resolution cell is relatively high.

Accordingly, based on above understanding, present invention provides an ultrasonic imaging system with a module for eliminating abnormal blood flow velocities. This module can judge the practical direction of blood flow intelligently by performing spatial-temporal smoothing only on the signs of blood flow velocities concurrently, so that the estimation error of blood flow direction caused by the system noise, clutter residue, speckle effect and etc. can be corrected.

Therefore, the method for eliminating abnormal blood flow velocities in a color flow image provided by present invention includes:

A. receiving signals of blood flow which are obtained by autocorrelation processing and include strength of blood flow, velocity of blood flow;

B. pre-processing the received signals to generate velocity signs in real time, each of the velocity signs corresponding to each pixel of the color flow image and indicating direction of blood flow at the corresponding pixel;

C. obtaining a plurality of the velocity signs in a predefined spatial and temporal order, which includes the velocity sign corresponding to a pixel to be confirmed, and performing weighted smoothing on the plurality of the velocity signs;

D. determining the direction of blood flow at the pixel to be confirmed according to result of the weighted smoothing.

In the above solution, the velocity signs obtained by preprocessing, are continuously stored frame by frame in time frame order, or the velocity signs are stored discontinuously frame by frame with predefined time frame interval.

In the above solution, all of the velocity signs corresponding to the pixels within a predefined area of a time frame are read out, wherein the predefined area includes the pixel to be confirmed and has predefined shape and aperture. Meanwhile, the velocity signs spatially corresponding to the pixel to be confirmed in adjacent multiple time frames are read out continuously. Then, all of the velocity signs read out from multiple time frames are subjected to weighted smoothing.

In the above solution, the pre-processing step includes: judging whether the received signals meet a predefined threshold; if the predefined threshold is met, outputting velocity sign of the pixel directly, otherwise outputting the result of the scan line smoothing as the velocity sign of the pixel.

In the above solution, the weighted smoothing processing includes: generating corresponding spatial-temporal weight factors according to parameters predefined by users and status parameters of system; weighted smoothing the obtained velocity signs by using the weight factors.

Other objects and attainments together with a fuller understanding of the invention will become apparent and appreciated by referring to the following description and claims taken in conjunction with the accompanying drawings.

BRIEF DESCRIPTION OF THE DRAWINGS

The invention is explained in further detail, and by way of example, with reference to the accompanying drawings wherein.

Throughout the drawings, the same reference numerals indicate similar or corresponding features or functions.

PREFERRED EMBODIMENTS OF THE INVENTION

The preferred embodiment of the present invention is described thoroughly in conjunction with drawings.

Figure 1:
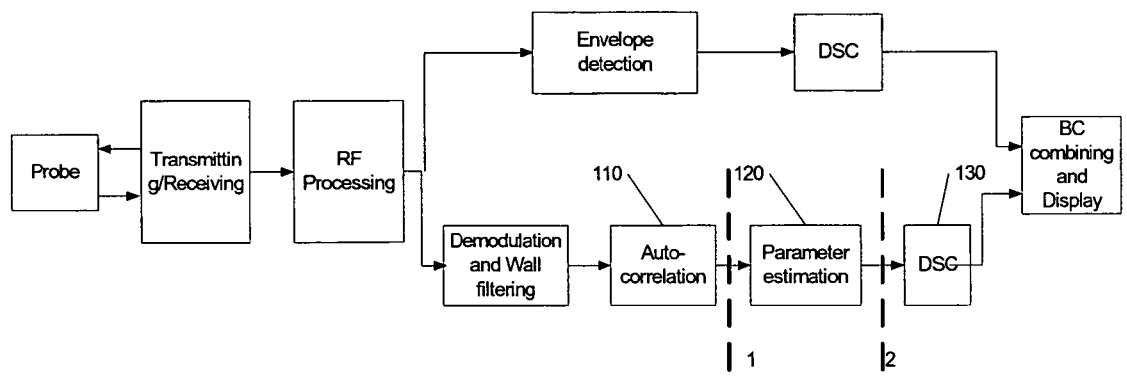
FIG. 1 is a block diagram illustrating a color flow imaging system in the prior art.

FIG. 1 is a block diagram showing the structure of a conventional color flow imaging system. As shown in FIG. 1, this system transmits a plurality of coherent pulses towards the interrogation area of a human body via a probe. The back-scattered waves of these pulses are received by the system. Then the received signals are divided into two branches after RF processing, which includes amplifying, filtering, analog-digital conversion and beam forming, etc. In one branch, the signals are fed to the processing channel of tissue imaging, and in the other branch, they are provided into the processing channel of color flow imaging. In the processing channel of tissue imaging, the generated data of tissue image are sent to display unit after envelope detection, logarithm compress processing and coordinate conversion, i.e. DSC (Digital Scan Conversion). In the processing channel of color flow imaging, the signals indicating strength, velocity and variance of blood flow are generated after orthogonal demodulation, wall filtering, auto-correlation processing (module 110) and parameter estimation (module 120). Next these signals are converted into the data of a color flow image by DSC 130, and then the converted data are sent into the display unit. At last, the data of blood flow image and that of tissue image are combined in the BC combining and displaying unit in order to be displayed on a screen.

Figure 2:
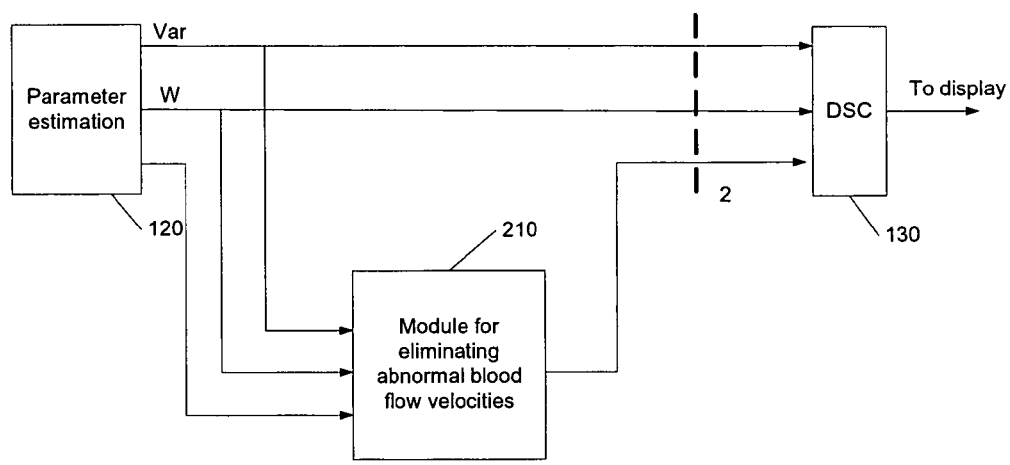
FIG. 2 is a schematic diagram showing a color flow imaging system with a module for eliminating abnormal blood velocities according to an embodiment of the present invention.
Figure 3:
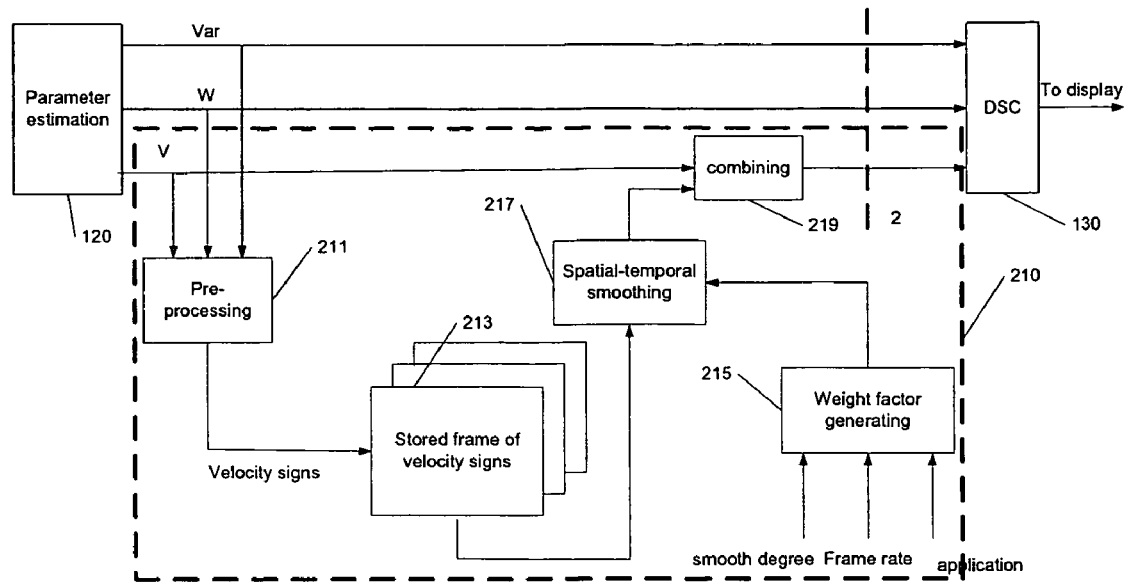
FIG. 3 is a schematic diagram illustrating the configuration of the module for eliminating abnormal blood velocities according to an embodiment of the present invention.

In the color flow imaging system as shown in FIG. 1, in order to show the direction of blood flow correctly as much as possible, the module 210 for eliminating abnormal blood flow velocities provided by present invention can be disposed between the parameter estimation module 120 and DSC 130 (i.e. at the dashed line 2), as shown in FIG. 2. In FIG. 2, the parameter estimation module 120 outputs the strength signal of blood flow W and the velocity signal of blood flow V, even the variance signal Var (if need) and these signals are sent to the module 210 for spatial-temporal smoothing, then module 210 outputs the blood flow velocities without abnormities (the detailed structure of module 210 is shown in FIG. 3). At the same time, strength signal W and variance signal Var output by the parameter estimation module 120 are sent to DSC130 directly, or sent to DSC130 via existing temporal (or spatial) smoothing module, so as to display a color flow image (Since the existing temporal or spatial smoothing is an optional technology, it is not shown in the figures and will not be mentioned in the following parts. But it is also within the scope of present invention). Furthermore, the module 210 for eliminating abnormal blood velocities can also be positioned after DSC 130. Since the signal processing in this situation is similar with FIG. 2 and FIG. 3, it will not be described in detail here.

Next, the structure and processing procedure of the module 210 provided by present invention will be described in detail in conjunction with FIGS. 3-7.

As shown in FIG. 3, the module 210 for eliminating abnormal blood flow velocities, which is set between parameter estimation module 120 and DSC 130, includes pre-processing unit 211, storing unit 213, weight factor generating unit 215, spatial-temporal smoothing unit 217, and combining unit 219. In module 210, pre-processing unit 211 is used to output the sign of blood flow velocity (or called velocity sign) corresponding to every pixel of the color flow image according to the signals W, V or Var in real time. Storing unit 213 is used to store the velocity signs in unit of a time frame. Weight factor generating unit 215 is used to generate and store the weight factors set by users or system. Spatial-temporal smoothing unit 217 is used to read out multiple velocity signs corresponding to the pixels within a predefined area of multiple time frames, and then performing spatial-temporal smoothing on the velocity signs by using the generated weight factors, so as to eliminate the abnormal blood flow velocities. Combining unit 219 is used for combining the velocity sign after spatial-temporal smoothing with the velocity signal estimated by parameter estimation module 120, so as to obtain the blood flow velocity without abnormity. The functions of these unites will be described in detail in the following.

Pre-Processing

In order to insure the reliability of the velocity sign of each pixel that involved in the spatial-temporal smoothing, according to the idea of present invention, scan line smoothing is firstly applied on the unreliable velocity signs in pre-processing unit 211. Then, the processed velocity sign is output as the result of this pixel. In present invention, the decision of velocity signs and scan line smoothing can both adopt various methods to realize.

For example, pre-processing unit 211 may compare the strength signal W with a predefined threshold (called the strength threshold). If strength signal W is greater than the strength threshold, the velocity sign of this pixel is output directly. Otherwise, the velocity sign of this pixel is regarded as unreliable, and then the result of scan line smoothing is output as the velocity sign of this pixel. In this case, pre-processing unit 211 only receives strength signal W and velocity signal V of blood flow while do not need receive the variance signal Var of blood flow. Additionally, the pre-defined strength threshold is the system noise floor in fact, and it is the strength curve output by the parameter estimation module 120 when the system transmitting circuit is turned off. This curve will be different based on the probe type, and different parts of human body, furthermore, it is generally obtained by experiments.

The pre-processing unit 211 may also compare the variance signal Var of blood flow with a pre-defined threshold (called variance threshold). If the variance signal Var is smaller than the variance threshold, velocity sign of this pixel is output directly. Otherwise, velocity sign of this pixel is the result of scan line smoothing.

The pre-processing unit 211 can also make a joint decision with strength signal W and variance Var of blood flow at the same time. For example, strength threshold and variance threshold are preset respectively. Only when W is greater than strength threshold and Var is smaller than variance threshold, velocity sign of this pixel is output directly. Otherwise, the output velocity sign of this pixel is the result of scan line smoothing. Of course, other joint decision method can be adopted in this invention. For example, the decision may be done by looking up a table. Since there are some existing technologies for reference, the detail description will be omitted here.

During the above decision process, scan line smoothing for unreliable velocity signs is to smooth the velocity signs of adjacent pixels along the scan line, and output the smoothed one as the velocity sign of the pixel. For example, it is convenient to select odd number of pixels (for example, but not limited to, 3, 5 or 7 pixels) to be smoothed. Then, the velocity sign that represents more than half of the velocity signs of these pixels (2, 3 or 4) will be output as the smoothed one.

Figure 4:
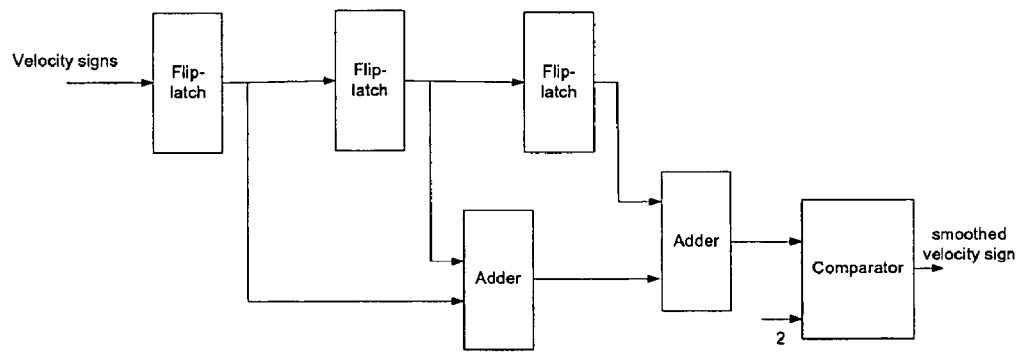
FIG. 4 is a block diagram showing the structure of a pre-processing unit for generating smoothed velocity signs according to an embodiment of the present invention.

Such smoothing can be realized by utilizing several flip-latches, adders and comparators. FIG. 4 shows an exemplary circuit for 3-pixel scan line smoothing. The velocity signs (indicated by 1 bit, wherein 1 represents forward direction and 0 represents backward direction) received in real time are feed into 3 flip-latches in series. The output of each flip-latch is summed up and then compared with a threshold (e.g. the value is 2) so as to determine the velocity sign accordant with those of more than half of the adjacent pixels.

The scan line smoothing may also use median filtering result of adjacent odd pixels along the scan line as the velocity sign of this pixel. Signals related to the blood flow velocity for each pixel go through median filtering and the velocity sign corresponding to the median filtering result is regarded as the velocity sign of this pixel.

Storing the Velocity Signs

The output velocity signs from pre-processing unit 211 can be stored in storing unit 213 in unit of time frame for further processing. Wherein, the number of velocity signs in each time frame is equal to the number of scan-lines multiplying with the number of resolution cells. The relevant time frames can be 3 to 7, or even larger. Taking 512 scan lines and 1024 resolution cells on each line as an example, the size of each time frame is 512×1024 bits. During storing, the velocity signs can be stored continuously frame by frame in time frame order. And it can also be stored discontinuously frame by frame with pre-defined time frame interval. For example, system can define the interval as 1 or 2 time frames to store the velocity signs generated in real time selectively.

Generating Weight Factors

The stored velocity signs are read out by spatial-temporal smoothing unit 217, and smoothed by using weight factors.

Herein, the weight factors come from weight factor generating unit 215. This unit receives smooth degree, parameters of specific application set by users, and status parameters such as the frame rate for system operating. Wherein, smooth degree mainly affects the number of pixels (i.e. aperture) for spatial smoothing and the number of time frames for temporal smoothing. Users can set these parameters through spatial smoothing item and temporal smoothing item in system menu or combination thereof. Frame rate mainly affects the number of time frames for temporal smoothing. When frame rate is high, the number of time frames involved in smoothing is large, and otherwise it is less. The specific application being tested determines the aperture and weight factors for spatial smoothing, and also the number of time frames and weight factors for temporal smoothing. For example, when the application is abdomen liver color flow imaging, the aperture of spatial smoothing needs to be larger. While for kidney imaging, in which blood vessel of artery and vein is thinner and the distribution of blood vessel is overlapped the aperture of spatial smoothing should be smaller. Taking femoral artery imaging as another example, since the blood flow in femoral artery will flow backward for an interval during a cardiac cycle; the number of time frames for temporal smoothing cannot be too large. Therefore, the proportion of weight factor for temporal smoothing is small in the whole weight factors.

Spatial-Temporal Smoothing

After the weight factors are obtained, spatial-temporal smoothing unit 217 reads out multiple velocity signs from storing unit 213 according to the predefined spatial and temporal order. And these multiple velocity signs are spatially and temporally smoothed by utilizing the weight factors output from the weight factor generating unit 215.

Wherein, spatial-temporal smoothing unit 217 reads the velocity signs of all pixels within a predefined area in one time frame, which are stored in the storing unit. The predefined area includes the pixels to be confirmed and has predefined shape and aperture. Additionally, spatial-temporal smoothing unit 217 also reads out the velocity signs of pixels accordant with the spatial coordinate of the pixels to be confirmed from adjacent several time frames.

Figure 5:
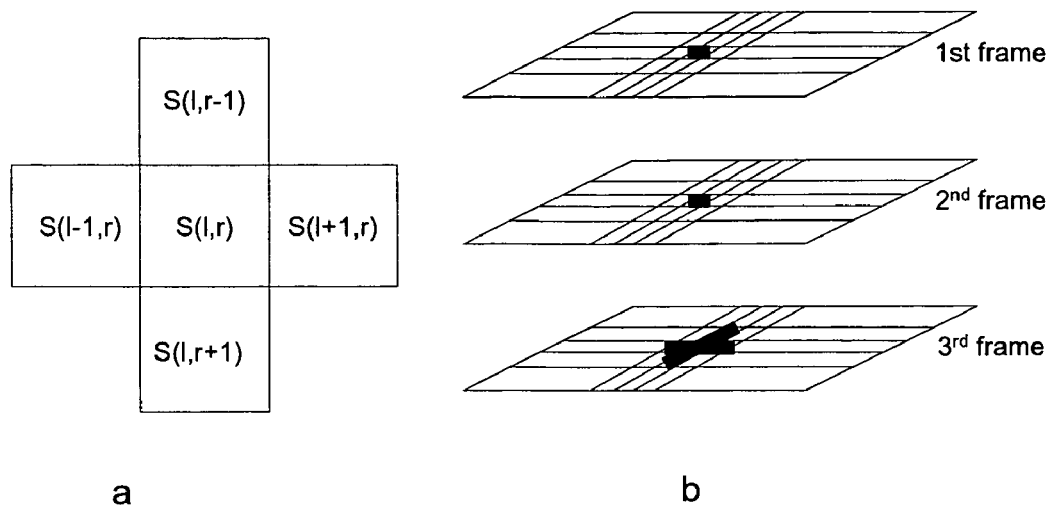
FIG. 5 is a schematic diagram showing the pixels' distribution when spatial-temporal smoothing is performed on velocity signs according to an embodiment of the present invention.

In order to state briefly, it is assumed that the pixel $S(l,r)$ shown in FIG. 5 (wherein, l represents scan line number; r represents resolution cell number; S represents velocity sign; S=0 for forward direction and S=1 for backward direction) is the one to be confirmed. Next, the spatial-temporal smoothing of present invention will be described in this assumption.

As shown in FIG. 5, the pixels involved in the spatial smoothing is set as 5 ones, which include the pixel to be confirmed and surrounded four adjacent pixels indicated by $S(l,r-1)$, $S(l-1,r)$, $S(l,r)$, $S(l+1,r)$ and $S(l,r+1)$ respectively (see "a" in FIG. 5). The pixels involved in the temporal smoothing is set as 3 pixels with the same coordinate as the pixel to be confirmed in 3 continuous time frames (see the black mark in "b" of FIG. 5).

After the aperture related to the spatial-temporal smoothing is determined, weight factor generating unit 215 generates weight factors (i.e. vector W) according to the parameters set by the users and the status parameters of the system, as shown by the equation below:

$$W=(W_s(1),W_s(2),W_s(3),W_s(4),W_s(5),W_t(1),W_t(2),W_t(3)) \quad (3)$$

Wherein, weight factor $W_s(1)$ corresponds to $S(l,r-1)$; $W_s(2)$ corresponds to $S(l-1,r)$; $W_s(3)$ corresponds to $S(l,r)$; $W_s(4)$ corresponds to $S(l+1,r)$; $W_s(1)$ corresponds to $S(l,r+1)$; $W_t(1)$, $W_t(2)$ and $W_t(3)$ are the weight factors corresponding to the pixel to be confirmed in the $1^{st}$, $2^{nd}$ and $3^{rd}$ frames respectively. The velocity signs corresponding to the pixel to be confirmed in $1^{st}$ and $2^{nd}$ frames can be set as $S(l,r+1)$ and $S''(l,r+1)$ respectively. Wherein, the sum of all the weight factors in vector W is 1.

Thereafter, the weighted sum $S_V$ is calculated according to the following equation:

$$S_V = W_s(1)*S(l,r-1) + W_s(2)*S(l-1,r) + W_s(3)*S(l,r) + W_s(4)*S(l+1,r) + W_s(5)*S(l,r+1) + W_t(1)*S'(l,r) + W_t(2)*S''(l,r) + W_t(3)*S(l,r)$$

Finally, the decision of velocity sign is made: (For example, but not limited to) if $S_V$ is less than the threshold of 0.5, the velocity sign of this pixel is set to 0 to indicate that the blood is flowing toward the probe; if $S_V$ is greater than 0.5, the velocity sign is set to 1, which indicates that the blood is flowing backward.

During the calculation of $S_V$, the sign of $S(l,r)$ has been used for twice. So the threshold value should be increased when make the decision. In practical system, two weight factors can be superposed to reduce the number of adders.

Figure 6:
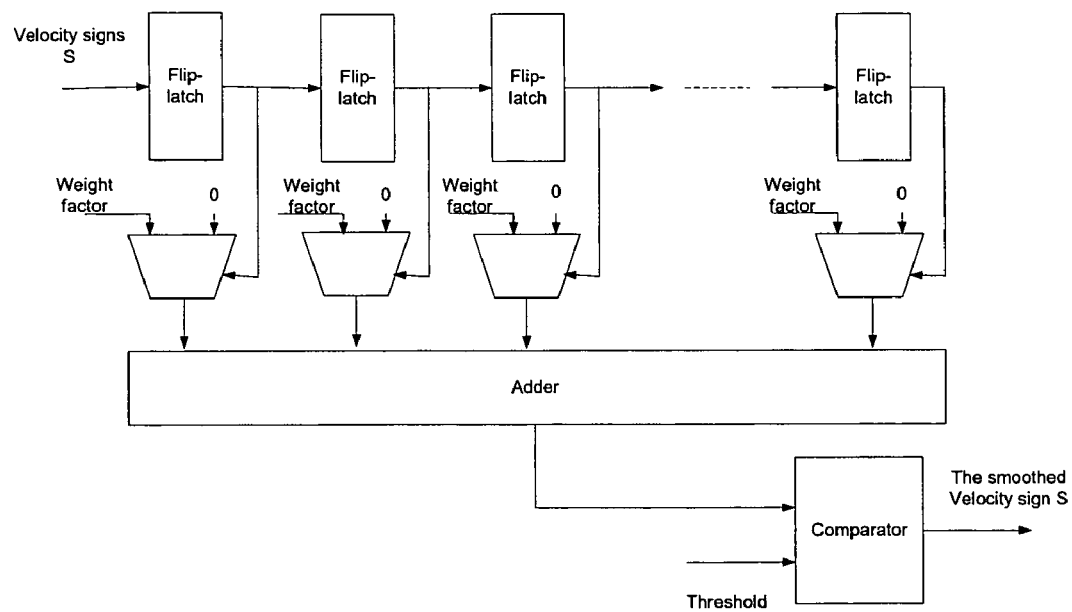
FIG. 6 is a block diagram illustrating the structure of the spatial-temporal smoothing unit implemented by using FIR filter according to an embodiment of the present invention.

A typical filtering process of FIR filter may be used to implement the calculation of $S_V$. Since the multiplier (velocity signs) of above multiplicator has only one bit, the multiplicator can be replaced with a multiplexer. If the calculation is implemented by FPGA (Field Programmable Gate Array), many multiplicators can be saved. FIG. 6 shows an exemplary circuit of present invention. For the pixel (l,r), the velocity signs are read out first as shown in FIG. 5, and then they are sent to the selecting end of each multiplexer. If the velocity sign is 0, the multiplexer outputs 0. If the velocity sign is 1, the multiplexer outputs the weight factor provided on the input end. The output of each multiplexer is sent to an adder. If the velocity signs of all the pixels involved in the spatial-temporal smoothing are read out, the output of the adder represents the probability of velocity with backward direction (backward). Finally, the decision of velocity sign is done. If the probability is greater than the threshold (for example 0.5), it indicates that the direction of blood flow velocity is backward and the comparator outputs 1. Otherwise, the comparator outputs 0.

Figure 7:
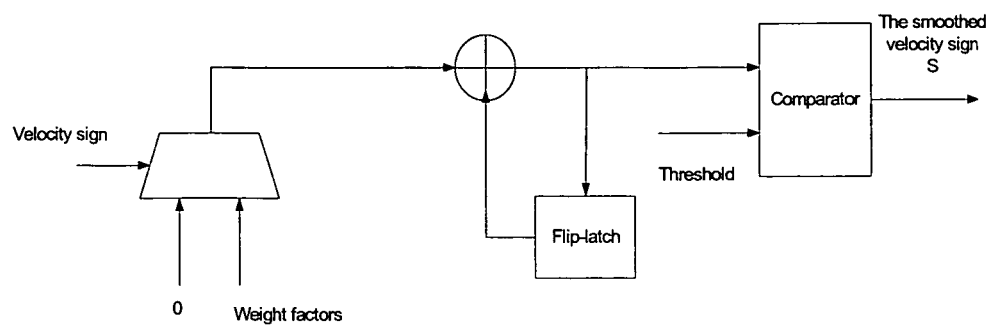
FIG. 7 is a schematic diagram illustrating the structure of the spatial-temporal smoothing unit according to another embodiment of the present invention.

Theoretically, the calculation of $S_V$ can also be realized with multiplier accumulator as shown in FIG. 7, and the multiplicator is also replaced with a multiplexer. The read velocity sign sequence controls the multiplexer in turn. 0 is on one input end of the multiplexer and another input end receives the weight factor generated by the weight factor generating unit. Each output of the multiplexer is sent to the adder for accumulation. Since the speed for data reading and selecting inside FPGA goes up to several hundreds MHz, the structure as shown in FIG. 6 and FIG. 7 allows as more pixels as possible to be involved in the spatial-temporal smoothing.

During the smoothing, the weight factors can be confirmed by looking up a table. It can also be confirmed by predefined formula and even by simpler weighting mode. For example, if the number of pixels involved in the spatial-temporal smoothing is N, all weight factors can be set to 1/N. In this way, the system described in FIG. 6 or FIG. 7 can be realized by only using flip-latches, adders and comparators and thereby the structure is more compact.

The working principle of the module for eliminating abnormal blood flow velocities is described in detail according to a preferred embodiment of the present invention together with drawings 3-7. But the present invention is not limited to this.

Figure 8:
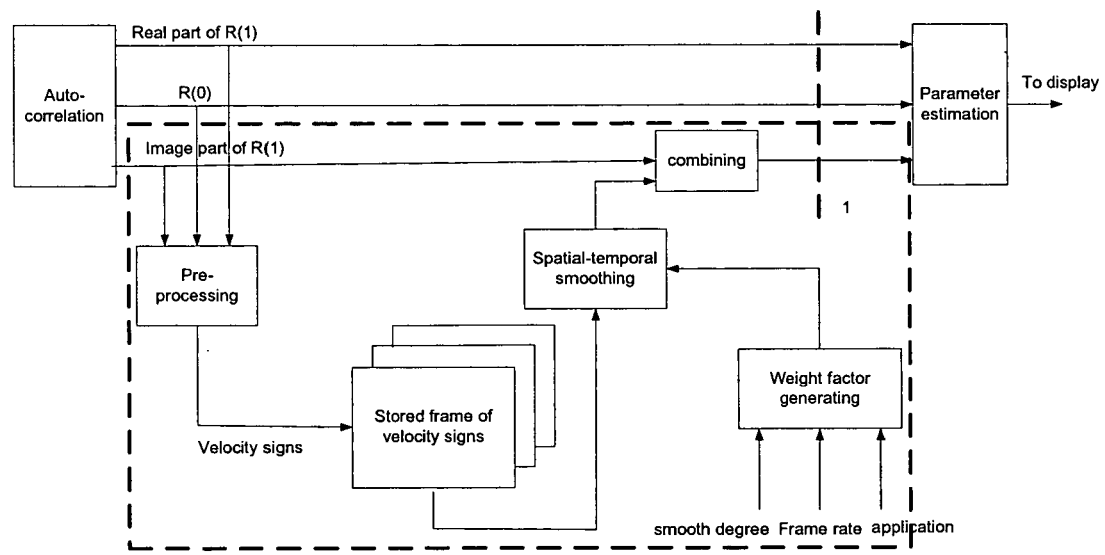
FIG. 8 is a block diagram showing a color flow imaging system with a module for eliminating abnormal blood velocities according to another embodiment of the present invention.
Figure 9:
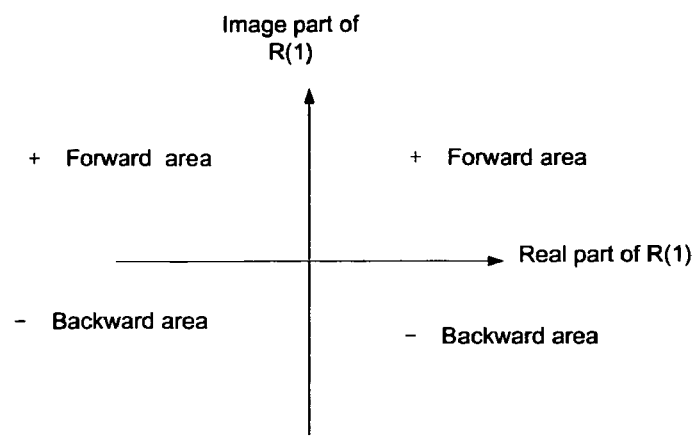
FIG. 9 illustrates the direction of blood flow corresponding to the imaginary part of first order correlation coefficient in signal domain according to another embodiment of the present invention.

As shown in FIG. 8, the module 210 of the present invention can also be disposed between the auto-correlation module 110 and the parameter estimation module 120 (i.e. at dashed line 1). In this situation, the module 210 receives the zero order and first order correlation coefficients, $R(0)$ and $R(1)$, of blood flow signals outputted from the auto-correlation module 110, and then processes the received signals. Wherein, $R(0)$ corresponds to the strength of blood flow; phase angle of $R(1)$ corresponds to the speed of blood flow; image part of $R(1)$ represents the direction of blood flow velocity as shown in FIG. 9. Since the weighted smoothing on the velocity signs of blood flow in FIG. 8 is same as that in FIG. 3, the detail description of FIG. 8 is omitted.

Figure 10:
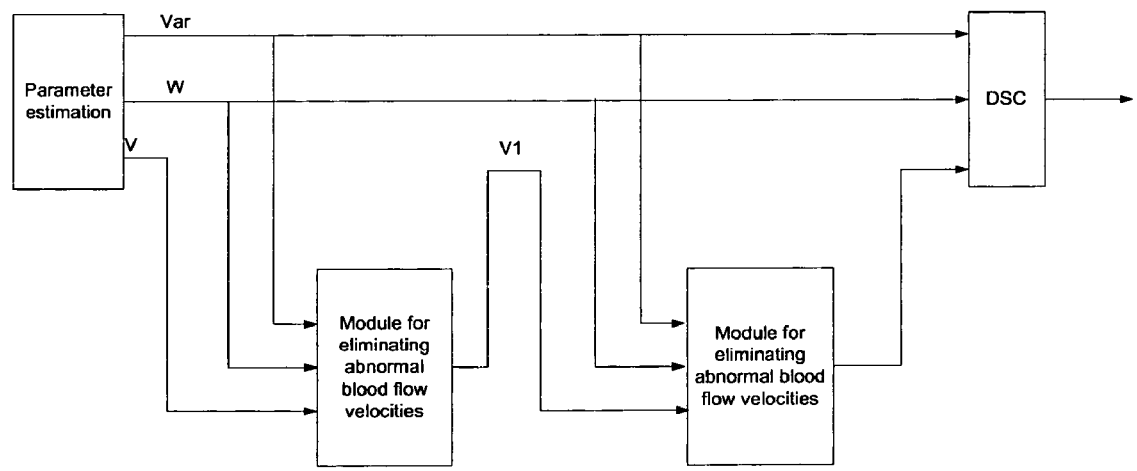
FIG. 10 is a schematic diagram illustrating a process for repeatedly using the module for eliminating abnormal blood velocities according to another embodiment of the present invention.

Furthermore, in order to increase the decision precision of the direction of blood flow in a color flow imaging system as much as possible, the method of present invention may be used repeatedly for several times as shown in FIG. 10. In FIG. 10, multiple modules 210 of the present invention can be connected in series so as to perform spatial-temporal smoothing on velocity signs for several times. In order to make it simple, the spatial-temporal smoothing for velocity signs in one of the modules can even be simplified as spatial smoothing or temporal smoothing further.

The present invention is described in detail with preferred embodiment. This solution provided by the present invention can eliminate abnormal velocities in a color flow image as much as possible so as to increase the precision and reliability of the detection for blood flow direction and make the color flow imaging apparatus more helpful to the clinic. Specifically, comparing with existing technologies, present invention has following advantages:

1. Since the spatial and temporal smoothing are applied on velocity signs of blood flow at the same time in the present invention, the basic discipline for periodicity and pulsation of blood flow in human body can be considered adequately;

2. Since the weight factors used in the smoothing of present invention is determined according to the blood flow discipline in different applications, it can be more flexible and reasonable to select the number of pixels involved in the spatial smoothing, the number of time frames involved in the temporal smoothing and the weight factors. Thus, the decision of velocity direction of blood flow is more scientific, macroscopical and reliable;

3. Only the signs of blood flow velocities (i.e. velocity signs) are smoothed with weight factors in the present invention. In this way, it will not result in the degradation of spatial resolution of images or signals, and furthermore the velocity direction of one point in a vessel can be detected for a long time. Thus, whether the abnormal velocity is aroused by turbulence can be judged more accurately than existing technologies (if it is, the sign of abnormal velocity in consecutive time frames should be consistent.).

4. The present invention adopts strength threshold decision in pre-processing. On one hand, it can prevent the unreliable velocity signs from being smoothed at certain degree. On the other hand, the signs of velocities blur due to Nyquist sampling limit can be retained.

5. In the present invention, only the velocity signs indicating the blood flow directions in a color flow image are stored and processed and then the system storage resource can be saved. Using a multiplexer to replace multiplier can save quite a lot of logical units required by multiplier processing. Thus, the system may process in real time and spend more time on blood flow observation to judge the direction of blood flow.

While the invention has been described in conjunction with specific embodiments, it is evident that many alternatives, modifications and variations will be apparent to those skilled in the art in light of the foregoing description. Accordingly, it is intended to embrace all such alternatives, modifications and variations as fall within the spirit and scope of the appended claims.

What is claimed is:

1. A method, used in an ultrasonic color imaging system, for eliminating abnormal blood flow velocities in a color flow image, comprising the steps of:
   A. receiving, from a parameter estimation module of the ultrasonic color imaging system, signals of blood flow which are obtained by auto-correlation processing and include strength and velocity of blood flow, wherein the velocity includes a speed and a direction of blood flow;
   B. pre-processing the received signals, using pre-processing circuitry of the ultrasonic color imaging system, to generate processed velocity signs in real time, each of the processed velocity signs corresponding to a respective pixel of the color flow image and indicating direction of blood flow at the corresponding pixel, wherein pre-processing the received signals comprises selectively changing indications of the direction of blood flow at each pixel based on a determination of reliability of the received signals and a comparison of velocity signs of adjacent pixels along a scan line, as either the direction of blood flow for the corresponding pixel indicated by the velocity included in the received signals or an opposite direction of blood flow for the corresponding pixel indicated by the velocity included in the received signals;
   C. obtaining, at spatial-temporal smoothing circuitry of the ultrasonic color imaging system, a plurality of the processed velocity signs in a predefined spatial area and temporal order corresponding to multiple time frames of the color flow image, which includes the processed velocity signs from the multiple time frames corresponding to a pixel to be confirmed, and performing weighted smoothing only on the plurality of the processed velocity signs without smoothing velocity magnitude values; and
   D. determining, using the spatial-temporal smoothing circuitry of the ultrasonic color imaging system, the direction of blood flow at the pixel to be confirmed according to a result of the weighted smoothing; and
   E. displaying a color on a display device at a location corresponding to the pixel to be confirmed, wherein the displayed color is based on the determined direction of blood flow at the pixel to be confirmed.

2. The method of claim 1, wherein the step B further comprises:
   B1. storing the plurality of the processed velocity signs according to a spatial and temporal order; and the step C further comprises:
   C1. reading the stored velocity signs according to the predefined spatial and temporal order.

3. The method of claim 2, wherein the step B1 comprises:
   storing the processed velocity signs frame by frame in time frame order; or
   storing the processed velocity signs frame by frame with a predefined time frame interval.

4. The method of claim 3, wherein the step of C1 comprises:
   reading the stored velocity signs corresponding to the pixels within a predefined area of a time frame, wherein the predefined area includes the pixel to be confirmed and has predefined shape and aperture; and
   reading the stored velocity signs spatially corresponding to the pixel to be confirmed in adjacent time frames.

5. The method of claim 1, wherein the pre-processing of step B comprises:
   judging whether the received signals meet a predefined threshold; and
   outputting, as the processed velocity sign, the direction of blood flow corresponding to a pixel directly indicated by the velocity included in the received signals if the predefined threshold is met, otherwise outputting the result of scan line smoothing as the processed velocity sign corresponding to the pixel.

6. The method of claim 5, wherein the judging step comprises:
   comparing the strength of blood flow with a strength threshold;
   wherein, if the strength of blood flow is greater than the strength threshold, the predefined threshold is met.

7. The method of claims 6, wherein the signals of blood flow further includes variance signal of blood flow, and
   comparing the variance signal of blood flow with a variance threshold,
   wherein, if the variance signal of blood flow is less than the variance threshold, the predefined threshold is met.

8. The method of claims 5, wherein the signals of blood flow further includes variance signal of blood flow, and
   comparing the variance signal of blood flow with a variance threshold,
   wherein, if the variance signal of blood flow is less than the variance threshold, the predefined threshold is met.

9. The method of claim 5, wherein the scan line smoothing comprises:
   outputting the processed velocity sign that represents the direction of blood flow, as indicated by the velocities included in the received signals, of more than half of the pixels including the pixel and adjacent pixels.

10. The method of claim 5, wherein the scan line smoothing comprises median filtering.

11. The method of claim 1, wherein the weighted smoothing comprises:
    generating corresponding spatial and temporal weight factors according to parameters set by users and status parameters of system; and
    performing weighted smoothing on the obtained velocity signs by using the weight factors.

12. The method of claim 11, wherein
    the parameters set by users comprise the aperture of spatial smoothing, time length of temporal smoothing, and interrogation body part; and
    the status parameters of system comprises frame rate.

13. The method of claims 11, wherein the weight factors are obtained by looking up a table.

14. The method of claim 1, wherein
    the received signals are the strength signals and velocity signals of blood flow in image domain obtained by parameter estimating, or by digital scan converting; or
    the received signals are the zero order and first order correlation coefficients of the signals of blood flow after auto-correlation processing in signal domain.

15. A module, used in an ultrasonic color imaging system, for eliminating abnormal blood flow velocities in a color flow image, comprising:
    a receiving unit configured for receiving signals of blood flow which are obtained by auto-correlation processing and include strength and velocity of blood flow, wherein the velocity includes a speed and a direction of blood flow;
    a pre-processing unit configured for pre-processing the received signals to generate processed velocity signs in real time, each of the processed velocity signs corresponding to a respective pixel of the color flow image and indicating direction of blood flow at the corresponding pixel, wherein the direction of blood flow indicated by each of the processed velocity signs is selected, based on a determination of reliability of the received signals, as either the direction of blood flow for the corresponding pixel indicated by the velocity included in the received signals or an opposite direction of blood flow for the corresponding pixel indicated by the velocity included in the received signals;

a spatial-temporal smoothing unit configured for obtaining a plurality of the processed velocity signs in a predefined spatial area and temporal order corresponding to multiple time frames of the color flow image, which includes the processed velocity sign from the multiple time frames corresponding to a pixel to be confirmed, and performing weighted smoothing only on the plurality of the processed velocity signs without smoothing velocity magnitude values; and a determining unit configured for determining the direction of blood flow at the pixel to be confirmed according to a result of the weighted smoothing.

16. The module of claim 15, further comprises:
a storing unit configured for storing the plurality of the processed velocity signs according to a spatial and temporal order; and the spatial-temporal smoothing unit further comprises a reading unit configured for reading the stored velocity signs according to the predefined spatial and temporal order.

17. The module of claim 16, wherein the storing unit is further configured for:
storing the processed velocity signs frame by frame in time frame order; or
storing the processed velocity signs frame by frame with a predefined time frame interval.

18. The module of claim 17, wherein the reading unit is further configured for reading the stored velocity signs corresponding to the pixels within a predefined area of a time frame, wherein the predefined area includes the pixel to be confirmed and has predefined shape and aperture, and wherein the reading unit is further configured for reading the stored velocity signs spatially corresponding to the pixel to be confirmed in adjacent time frames.

19. The module of claim 16, further comprises:
a weight factor generating unit configured for generating corresponding spatial and temporal weight factors according to parameters set by users and status parameters of system;
wherein the spatial-temporal smoothing unit performs weighted smoothing on the obtained velocity signs by using the weight factors.

20. The module of claim 19, wherein the spatial-temporal smoothing unit further comprises:
at least a multiplexer, controlled by the read velocity signs, wherein zero is supplied to one input end of each multiplexer, and the another input end receives the weight factor generated by the weight factor generating unit; and
an adder configured for accumulating the output of the at least multiplexer.

21. The module of claim 15, wherein the pre-processing unit further comprises:
a judging unit configured for judging whether the received signals meet a predefined threshold; and
an output unit configured for outputting, as the processed velocity sign, the direction of blood flow corresponding to a pixel directly indicated by the velocity included in the received signals if the predefined threshold is met, otherwise outputting the result of scan line smoothing as the velocity sign corresponding to the pixel.

22. The module of claim 15, wherein
the receiving unit is configured for receiving strength signals and velocity signals of blood flow in image domain obtained by parameter estimating, or by digital scan converting; or
the receiving unit is configured for receiving zero order and first order correlation coefficients of the signals of blood flow after auto-correlation processing in signal domain.

23. An ultrasonic color flow imaging system comprising the module of claim 15, wherein the ultrasonic color flow imaging system uses the module to eliminate the abnormal blood flow velocities in a color flow image.

* * * * *